United States Patent
Barta et al.

(10) Patent No.: US 8,188,331 B2
(45) Date of Patent: May 29, 2012

(54) SEE-THROUGH, REDUCED-PRESSURE DRESSINGS AND SYSTEMS

(75) Inventors: Eric Woodson Barta, San Antonio, TX (US); Justin Alexander Long, San Antonio, TX (US); Richard Marvin Kazala, Jr., San Antonio, TX (US); Matthew Francis Cavanaugh, II, San Antonio, TX (US); Michael Girouard, San Antonio, TX (US); Kenneth Mitchel Knowles, Bandera, TX (US)

(73) Assignee: KCI Licensing, Inc., San Antonio, TX (US)

( * ) Notice: Subject to any disclaimer, the term of this patent is extended or adjusted under 35 U.S.C. 154(b) by 301 days.

(21) Appl. No.: 12/475,380

(22) Filed: May 29, 2009

(65) Prior Publication Data

US 2009/0299256 A1     Dec. 3, 2009

Related U.S. Application Data

(60) Provisional application No. 61/057,807, filed on May 30, 2008, provisional application No. 61/057,798, filed on May 30, 2008, provisional application No. 61/057,808, filed on May 30, 2008, provisional application No. 61/057,802, filed on May 30, 2008, provisional application No. 61/057,803, filed on May 30, 2008, provisional application No. 61/057,800, filed on May 30, 2008, provisional application No. 61/057,797, filed on May 30, 2008, provisional application No. 61/057,805, filed on May 30, 2008, provisional application No. 61/057,810, filed on May 30, 2008, provisional application No. 61/121,362, filed on Dec. 10, 2008, provisional application No. 61/144,067, filed on Jan. 12, 2009.

(51) Int. Cl.
    *A61F 13/06*        (2006.01)
    *A61F 13/00*        (2006.01)
    *A61M 1/00*        (2006.01)

(52) U.S. Cl. .......................... 602/53; 604/317; 424/443

(58) Field of Classification Search .............. 602/41–48, 602/52–56, 58–60; 604/317, 358, 367, 369, 604/378, 381, 382, 383; 424/447, 448, 443, 424/449

See application file for complete search history.

(56) References Cited

U.S. PATENT DOCUMENTS 1,195,430 A     8/1916     Angier
(Continued)

FOREIGN PATENT DOCUMENTS

AU     550575 A1     8/1982
(Continued)

OTHER PUBLICATIONS

International Search Report and Written Opinion date mailed Mar. 12, 2010; PCT International Application No.: PCT/US2009/045755.

(Continued)

*Primary Examiner* — Kim M Lewis
*Assistant Examiner* — Tarla Patel
(74) *Attorney, Agent, or Firm* — SNR Denton US, LLP

(57) ABSTRACT

A see-through dressing assembly is presented for use with a reduced-pressure system for treating a wound on a patient using reduced pressure that allows visual observation of the wound during treatment. The dressing assembly includes a bolster for providing a directed force when under reduced pressure, a sealing member for covering the bolster and providing a seal over the bolster and a patient's epidermis, and wherein the bolster and sealing member are formed from see-through materials sufficient to allow perception of color from a point external to the system. Other systems, dressings, and methods are presented.

12 Claims, 9 Drawing Sheets

U.S. PATENT DOCUMENTS

| | | |
|---|---|---|
| 1,355,846 A | 10/1920 | Rannells |
| 1,845,630 A | 2/1932 | Scholl |
| 2,452,345 A | 10/1948 | Anselmo |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,026,874 A | 3/1962 | Stevens |
| 3,066,672 A | 12/1962 | Crosby, Jr. et al. |
| 3,367,332 A | 2/1968 | Groves |
| 3,419,006 A | 12/1968 | King |
| 3,520,300 A | 7/1970 | Flower, Guiles, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 3,892,229 A | 7/1975 | Taylor et al. |
| 4,080,970 A | 3/1978 | Miller |
| 4,091,804 A | 5/1978 | Hasty |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,224,945 A | 9/1980 | Cohen |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,266,545 A | 5/1981 | Moss |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,375,217 A | 3/1983 | Arkans |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,722,332 A | 2/1988 | Saggers |
| 4,727,868 A | 3/1988 | Szycher et al. |
| 4,733,659 A | 3/1988 | Edenbaum et al. |
| 4,743,232 A | 5/1988 | Kruger |
| 4,758,220 A | 7/1988 | Sundblom et al. |
| 4,770,490 A | 9/1988 | Gruenewald et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,902,565 A | 2/1990 | Brook et al. |
| 4,906,233 A | 3/1990 | Moriuchi et al. |
| 4,906,240 A | 3/1990 | Reed et al. |
| 4,917,112 A | 4/1990 | Kalt |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,000,741 A | 3/1991 | Kalt |
| 5,018,515 A * | 5/1991 | Gilman ........................... 602/52 |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,106,629 A | 4/1992 | Cartmell et al. |
| 5,134,994 A | 8/1992 | Say |
| 5,149,331 A | 9/1992 | Ferdman et al. |
| 5,160,315 A | 11/1992 | Heinecke et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,380,294 A | 1/1995 | Persson |
| 5,423,737 A | 6/1995 | Cartmell et al. |
| 5,429,593 A | 7/1995 | Matory |
| 5,435,009 A | 7/1995 | Schild et al. |
| 5,437,622 A | 8/1995 | Carion |
| 5,437,651 A | 8/1995 | Todd et al. |
| 5,489,262 A | 2/1996 | Cartmell et al. |
| 5,497,788 A | 3/1996 | Inman et al. |
| 5,520,629 A | 5/1996 | Heinecke et al. |
| 5,527,293 A | 6/1996 | Zamierowski |
| 5,538,502 A | 7/1996 | Johnstone |
| 5,549,584 A | 8/1996 | Gross |
| 5,556,375 A | 9/1996 | Ewall |
| 5,607,388 A | 3/1997 | Ewall |
| 5,628,230 A | 5/1997 | Flam |
| 5,636,643 A | 6/1997 | Argenta et al. |
| 5,645,081 A | 7/1997 | Argenta et al. |
| 5,653,244 A | 8/1997 | Shaw et al. |
| 5,792,088 A | 8/1998 | Felder et al. |
| 5,844,013 A | 12/1998 | Kenndoff et al. |
| 5,866,249 A | 2/1999 | Yarusso et al. |
| 5,950,238 A | 9/1999 | Klein |
| 6,071,267 A | 6/2000 | Zamierowski |
| 6,086,450 A | 7/2000 | Mankovitz |
| 6,109,267 A | 8/2000 | Shaw et al. |
| 6,135,116 A | 10/2000 | Vogel et al. |
| 6,162,960 A | 12/2000 | Klein |
| 6,213,840 B1 | 4/2001 | Han |
| 6,241,747 B1 | 6/2001 | Ruff |
| 6,270,910 B1 | 8/2001 | Jaeger et al. |
| 6,287,316 B1 | 9/2001 | Agarwal et al. |
| 6,345,623 B1 | 2/2002 | Heaton et al. |
| 6,361,397 B1 | 3/2002 | Mankovitz et al. |
| 6,420,622 B1 | 7/2002 | Johnston et al. |
| 6,440,093 B1 | 8/2002 | McEwen et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,648,862 B2 | 11/2003 | Watson |
| 6,685,681 B2 | 2/2004 | Lockwood et al. |
| 6,752,794 B2 | 6/2004 | Lockwood et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,867,342 B2 | 3/2005 | Johnston et al. |
| D503,509 S | 4/2005 | Bell et al. |
| 6,936,037 B2 | 8/2005 | Bubb et al. |
| 6,951,553 B2 | 10/2005 | Bubb et al. |
| 7,004,915 B2 | 2/2006 | Boynton et al. |
| 7,070,584 B2 | 7/2006 | Johnson et al. |
| 7,090,647 B2 | 8/2006 | Mimura et al. |
| 7,135,007 B2 | 11/2006 | Scott et al. |
| 7,144,294 B2 | 12/2006 | Bell et al. |
| 7,195,624 B2 | 3/2007 | Lockwood et al. |

| | | | |
|---|---|---|---|
| 7,201,063 B2 | 4/2007 | Taylor | |
| 7,201,263 B2 | 4/2007 | Osada et al. | |
| 7,214,202 B1 | 5/2007 | Vogel et al. | |
| 7,316,672 B1 | 1/2008 | Hunt et al. | |
| 7,361,184 B2 | 4/2008 | Joshi | |
| 7,455,681 B2 | 11/2008 | Wilke et al. | |
| 7,504,549 B2 | 3/2009 | Castellani et al. | |
| 7,520,872 B2 | 4/2009 | Biggie et al. | |
| 7,532,953 B2 | 5/2009 | Vogel | |
| 7,569,742 B2 | 8/2009 | Haggstrom | |
| 7,699,831 B2 | 4/2010 | Bengtson et al. | |
| 8,100,848 B2 | 1/2012 | Wilkes et al. | |
| 2001/0029956 A1 | 10/2001 | Argenta et al. | |
| 2001/0043943 A1* | 11/2001 | Coffey | 424/447 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0040691 A1 | 2/2003 | Griesbach et al. | |
| 2003/0109816 A1 | 6/2003 | Lachenbruch et al. | |
| 2003/0212359 A1* | 11/2003 | Butler | 602/48 |
| 2004/0039415 A1 | 2/2004 | Zamierowski | |
| 2004/0064111 A1 | 4/2004 | Lockwood et al. | |
| 2004/0064132 A1 | 4/2004 | Boehringer et al. | |
| 2004/0242119 A1 | 12/2004 | Francis | |
| 2004/0243073 A1 | 12/2004 | Lockwood | |
| 2005/0209574 A1 | 9/2005 | Boehringer et al. | |
| 2005/0222544 A1 | 10/2005 | Weston | |
| 2005/0228329 A1 | 10/2005 | Boehringer et al. | |
| 2006/0041247 A1 | 2/2006 | Petrosenko et al. | |
| 2006/0064049 A1 | 3/2006 | Marcussen | |
| 2006/0079852 A1 | 4/2006 | Bubb et al. | |
| 2006/0149171 A1 | 7/2006 | Vogel et al. | |
| 2006/0173253 A1 | 8/2006 | Ganapathy | |
| 2006/0189910 A1 | 8/2006 | Johnson et al. | |
| 2006/0213527 A1 | 9/2006 | Argenta et al. | |
| 2006/0264796 A1 | 11/2006 | Flick et al. | |
| 2007/0021697 A1 | 1/2007 | Ginther | |
| 2007/0027414 A1 | 2/2007 | Hoffman et al. | |
| 2007/0066946 A1 | 3/2007 | Haggstrom et al. | |
| 2007/0078366 A1 | 4/2007 | Haggstrom et al. | |
| 2007/0135777 A1 | 6/2007 | Greene et al. | |
| 2007/0185426 A1 | 8/2007 | Ambrosio et al. | |
| 2007/0219497 A1 | 9/2007 | Johnson | |
| 2007/0219513 A1 | 9/2007 | Lina et al. | |
| 2007/0219532 A1 | 9/2007 | Karpowicz et al. | |
| 2008/0004549 A1 | 1/2008 | Anderson et al. | |
| 2008/0009812 A1 | 1/2008 | Riesinger et al. | |
| 2008/0039763 A1 | 2/2008 | Sigurjonsson et al. | |
| 2008/0076844 A1 | 3/2008 | Van Sumeren et al. | |
| 2009/0043268 A1 | 2/2009 | Eddy et al. | |
| 2009/0177051 A1 | 7/2009 | Arons et al. | |
| 2009/0204084 A1 | 8/2009 | Blott et al. | |
| 2009/0204085 A1 | 8/2009 | Biggie et al. | |
| 2009/0227968 A1 | 9/2009 | Vess | |
| 2009/0234307 A1 | 9/2009 | Vitaris | |
| 2009/0264807 A1 | 10/2009 | Haggstrom | |
| 2009/0293887 A1 | 12/2009 | Wilkes et al. | |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 26 40 413 A1 | 3/1978 |
| DE | 39 07 522 C1 | 4/1990 |
| DE | 43 06 478 A1 | 9/1994 |
| DE | 295 04 378 U1 | 10/1995 |
| DE | 20 2006 00787 | 7/2006 |
| DE | 10 2005 00701 A1 | 8/2006 |
| EP | 0100148 A1 | 2/1984 |
| EP | 0117632 A2 | 9/1984 |
| EP | 0161865 A2 | 11/1985 |
| EP | 0330373 A2 | 8/1989 |
| EP | 0358302 A2 | 3/1990 |
| EP | 0424165 A1 | 4/1991 |
| EP | 0691113 A1 | 1/1996 |
| EP | 1018967 B1 | 8/2004 |
| FR | 1163907 A | 10/1958 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 95/14451 A1 | 6/1995 |
| WO | WO 96/05873 | 2/1996 |
| WO | WO 97/18007 | 5/1997 |
| WO | WO 99/13793 | 3/1999 |
| WO | WO 00/07653 A1 | 2/2000 |
| WO | WO 03/057071 A2 | 7/2003 |
| WO | WO 03/057307 A1 | 7/2003 |
| WO | WO 03/086262 A2 | 10/2003 |
| WO | WO 2005123170 A1 | 12/2005 |
| WO | WO 2006/012745 A1 | 2/2006 |
| WO | WO 2007/031762 | 3/2007 |
| WO | WO 2007/033679 | 3/2007 |
| WO | WO 2007/041642 A2 | 4/2007 |
| WO | WO 2008/054312 A1 | 5/2008 |
| WO | WO 2008/063281 A2 | 5/2008 |
| WO | WO 2009/019496 A2 | 2/2009 |
| WO | WO 2009/047524 A2 | 4/2009 |
| WO | WO 2009/071926 A1 | 6/2009 |

OTHER PUBLICATIONS

N. A. Bagautdinov, "Variant of External Vacuum Aspiration in the Treatment of Purulent Diseases of the Soft Tissues," *Current Problems in Modem Clinical Surgery: Interdepartmental Collection*, edited by V. Ye Volkov et al. (Chuvashia State University, Cheboksary, U.S.S.R. 1986);pp. 94-96 (copy and certified translation).

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/G698/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: " A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: "New and Established Methods, *Chronic Wound Care*, edited by D. Krasner (Health Management Publications, Inc., King of Prussia, PA 1990), pp. 240-246.
G. Živadinović, V. Đukić, Ž. Maksimović, Đ. Radak, and P. Peŝska, "Vacuum Therapy in the Treatment of Peripheral Blood Vessels," *Timok Medical Journal* 11 (1986), pp. 161-164 (copy and certified translation).
F.E. Johnson, "An Improved Technique for Skin Graft Placement Using a Suction Drain," *Surgery, Gynecology, and Obstetrics* 159 (1984), pp. 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," *British Journal of Surgery* 73 (1986), pp. 369-370.
D.E. Tribble, An Improved Sump Drain-Irrigation Device of Simple Construction, *Archives of Surgery* 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).
C.E. Tennants, "The Use of Hypermia in the Postoperative Treatment of Lesions of the Extremities and Thorax, " *Journal of the American Medical Association* 64 (1915), pp. 1548-1549.
Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988)("Solovev Abstract").
Product Information for OptSite™ dressing.
Non-Final Rejection mailed Jul. 20, 2011 for U.S. Appl. No. 12/475,301.
Restriction Requirement mailed May 10, 2011 for U.S. Appl. No. 12/475,285.
Response to Restriction Requirement filed Jun. 7, 2011 for U.S. Appl. No. 12/475,285.
Non-Final Rejection mailed Aug. 19. 2011 for U.S. Appl. No. 12/475,285.
Restriction Requirement mailed May 10, 2011 for U.S. Appl. No. 12/475,367.
Response to Restriction Requirement filed Jun. 7, 2011 for U.S. Appl. No. 12/475,367.
Non-Final Rejection mailed Aug. 23, 2011 for U.S. Appl. No. 12/475,367.
Restriction Requirement mailed May 17, 2011 for U.S. Appl. No. 12/475,319.
Response to Restriction Requirement filed Jun. 7, 2011 for U.S. Appl. No. 12/475,319.
Non-Final Rejection mailed Aug. 18, 2011 for U.S. Appl. No. 12/475,319.
Non-Final Rejection mailed May 24, 2011 for U.S. Appl. No. 12/475,257.
Response to Non-Final Rejection filed Jul. 27, 2011 for U.S. Appl. No. 12/475,257.
Restriction Requirement mailed May 9, 2011 for U.S. Appl. No. 12/475,388.
Response to Restriction Requirement filed Jun. 7, 2011 for U.S. Appl. No. 12/475,388.
Non-Final Rejection mailed Sep. 7, 2011 for U.S. Appl. No. 12/475,388.
Restriction Requirement mailed Apr. 29, 2011 for U.S. Appl. No. 12/475,231.
Response to Restriction Requirement filed May 19, 2011 for U.S. Appl. No. 12/475,231.
Non-Final Rejection mailed Sep. 6, 2011 for U.S. Appl. No. 12/475,231.
Restriction Requirement mailed May 12, 2011 for U.S. Appl. No. 12/475,407.
Response to Restriction Requirement filed Jun. 7, 2011 for U.S. Appl. No. 12/475,407.
Non-Final Rejection mailed Aug. 23, 2011 for U.S. Appl. No. 12/475,407.
Restriction Requirement mailed May 9, 2011 for U.S. Appl. No. 12/475,373.
Response to Restriction Requirement filed Jun. 7, 2011 for U.S. Appl. No. 12/475,373.
Non-Final Rejection mailed Aug. 23, 2011 for U.S. Appl. No. 12/475,373.
Laskin, et al.; "Minimally Invasive Total Knee Replacement Through a Mini-Midvastus Incision: An Outcome Study," Surgical Technology International XIII, 2004; 231-8.
A. Dee, "The successful management of a dehisced surgical wound with TNP following Femoropopliteal bypass", Journal of Wound Care, vol. 16, No. 1, Jan. 2007.
Ogazon, Use of Vacuum-Assisted Closure in the Treatment of Surgical Infection Sites Cir. Mar.-Apr. 2006; 74(2): 107-13 (Spanish).
Timmenga, "The Effects of Mechanical Stress on Healing Skin Wounds: An Experimental Study in Rabbits Using Tissues Expansions," British Journal of Plastic Surgery 1991; 44(7): 514-519.
Cunningham "Development of in-vitro Model to Simulate Dermal Wound Bed Interaction with GranuFoam and Gauze Dressing under Sub Atmospheric Pressure" RPT 111-05-02, Device Implant Innovations 2006.
Delalleau, A., et al, "Characterization of the Mechanical Properties of Skin by Inverse Analysis Combined with the Indentation Test" Journal of Biomechanics, 2006; pp. 1603-1610.

Pailler-Mattei, C., "Caracte; Risation Me' Canique et Tribologizue de la Peau Humain In Vivo", 2004-31.

Khatyr, F., "Model of the Viscoelastic Behavior of Skin In Vivo and Study of Anisotropy", Skin Research and Technology 2004; pp. 96-103.

Wilkes, "3D Strain Measurement in Soft Tissue: Demonstration of a Novel Inverse Finite Element Model Algorithm on MicroCT Images of a Tissue Phantom Exposed to Negative Pressure Wound Therapy," Journal of the Mechanical Behavior of Biomedical Materials (2008), pp: 1-16.

Diridollou, "In vivo Model of the Mechanical Properties of the Human Skin under Suction", Skin Research and Technology, 2000; 6:214-221.

Woo, "Structural Model to Describe the Non-Linear Stress-Strain Behavior for Parallel-Fibered Collagenous Tissues," Journal of Biomechanical Engineering, Nov. 1989, vol. 111/361.

International Search Report and Written Opinion date mailed Oct. 20, 2009; PCT International Application No. PCT/US2009/045747.

International Search Report and Written Opinion date mailed Oct. 16, 2009; PCT International Application No. PCT/US2009/045752.

Partial International Search Report and Written Opinion date mailed Oct. 7, 2009; PCT International Application No. PCT/US2009/045755.

International Search Report and Written Opinion date mailed Oct. 14, 2009; PCT International Application No. PCT/US2009/045746.

International Search Report and Written Opinion date mailed Oct. 27, 2009; PCT International Application No. PCT/US2009/045744.

Partial International Search Report and Written Opinion date mailed Oct. 19, 2009; PCT International Application No. PCT/US2009/045742.

International Search Report and Written Opinion date mailed Oct. 26, 2009; PCT International Application No. PCT/US2009/045751.

Partial Search Report date mailed Nov. 2, 2009; PCT International Application No. PCT/US2009/045750.

International Search Report and Written Opinion date mailed Nov. 11, 2009; PCT International Application No. PCT/US2009/045754.

International Search Report and Written Opinion date mailed Oct. 21, 2009; PCT International Application No. PCT/US2009/045749.

International Search Report and Written Opinion date mailed Dec. 11, 2009; PCT International Application No. PCT/US2009/045753.

International Search Report and Written Opinion date mailed Feb. 25, 2010; PCT International Application No. PCT/US2009/045750.

International Search Report and Written Opinion date mailed Aug. 30, 2011 for PCT International Application No. PCT/US2011/034300.

Response filed Oct. 20, 2011 for U.S. Appl. No. 12/475,285.

Interview Summary date mailed Oct. 26, 2011 for U.S. Appl. No. 12/475,285.

Non-Final Office Action date mailed Sep. 15, 2011 for U.S. Appl. No. 12/475,398.

Response filed Oct. 5, 2011 for U.S. Appl. No. 12/475,301.

Response filed Oct. 18, 2011 for U.S. Appl. No. 12/475,367.

Response filed Oct. 20, 2011 for U.S. Appl. No. 12/475,319.

Interview Summary date mailed Oct. 26, 2011 for U.S. Appl. No. 12/475,319.

Restriction Requirement date mailed Oct. 12, 2011 for U.S. Appl. No. 12/475,328.

Response filed Oct. 19, 2011 for U.S. Appl. No. 12/475,328.

Notice of Allowance date mailed Sep. 16, 2011 for U.S. Appl. No. 12/475,257.

Response filed Oct. 20, 2011 for U.S. Appl. No. 12/475,407.

Interview Summary date mailed Oct. 27, 2011 for U.S. Appl. No. 12/475,407.

Response filed Oct. 25, 2011 for U.S. Appl. No. 12/475,373.

Interview Summary date mailed Oct. 27, 2011 for U.S. Appl.No. 12/475,373.

Non-Final Office Action date mailed Dec. 28, 2011 for U.S. Appl. No. 12/475,285.

Response filed Nov. 22, 2011 for U.S. Appl. No. 12/475,398.

Interview Summary date mailed Nov. 29, 2011 for U.S. Appl. No. 12/475,398.

Notice of Allowance date mailed Nov. 14, 2011 for U.S. Appl. No. 12/475,301.

Notice of Allowance date mailed Jan. 3, 2012 for U.S. Appl. No. 12/475,319.

Non-Final Office Action date mailed Dec. 9, 2011 for U.S. Appl. No. 12/475,328.

Response filed Nov. 11, 2011 for U.S. Appl. No. 12/475,388.

Interview Summary date mailed Dec. 5, 2011 for U.S. Appl. No. 12/475,388.

Response filed Nov. 11, 2011 for U.S. Appl. No. 12/475,231.

Interview Summary date mailed Dec. 5, 2011 for U.S. Appl. No. 12/475,231.

Notice of Allowance date mailed Jan. 9, 2012 for U.S. Appl. No. 12/475,407.

Response filed Feb. 9, 2012 for U.S. Appl. No. 12/475,328.

Notice of Allowance date mailed Feb. 17, 2012 for U.S. Appl. No. 12/475,388.

Notice of Allowance date mailed Jan. 20, 2012 for U.S. Appl. No. 12/475,231.

Notice of Allowance date mailed Jan. 10, 2012 for U.S. Appl. No. 12/475,373.

* cited by examiner

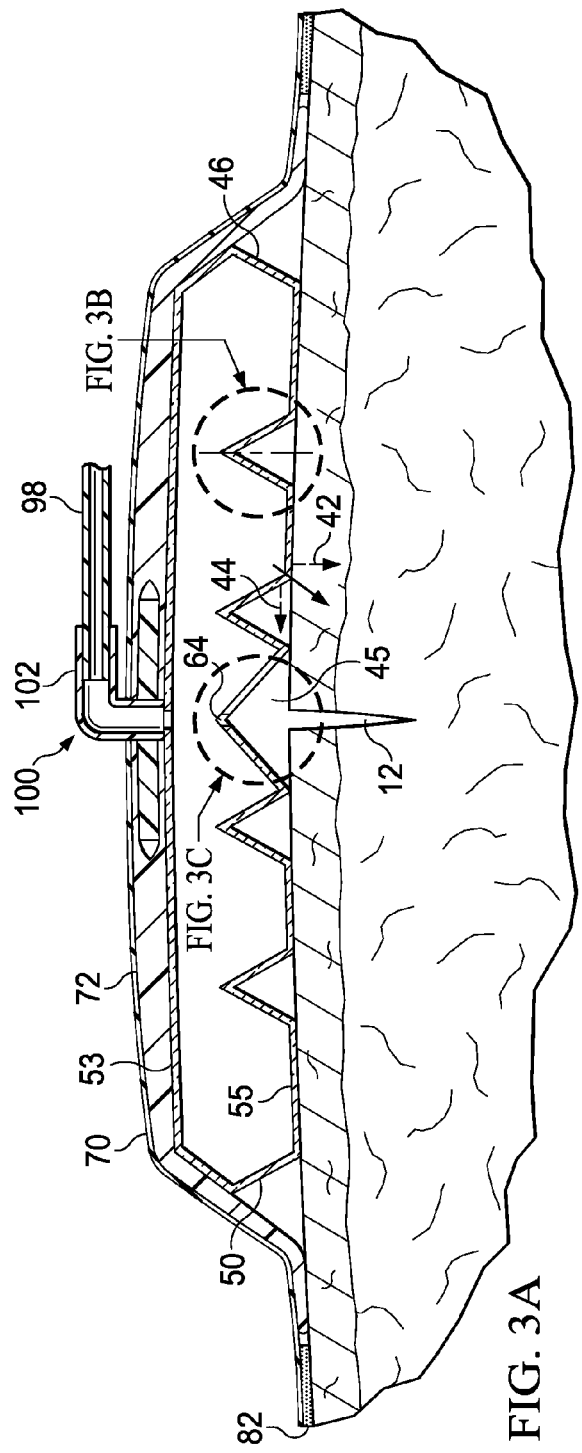
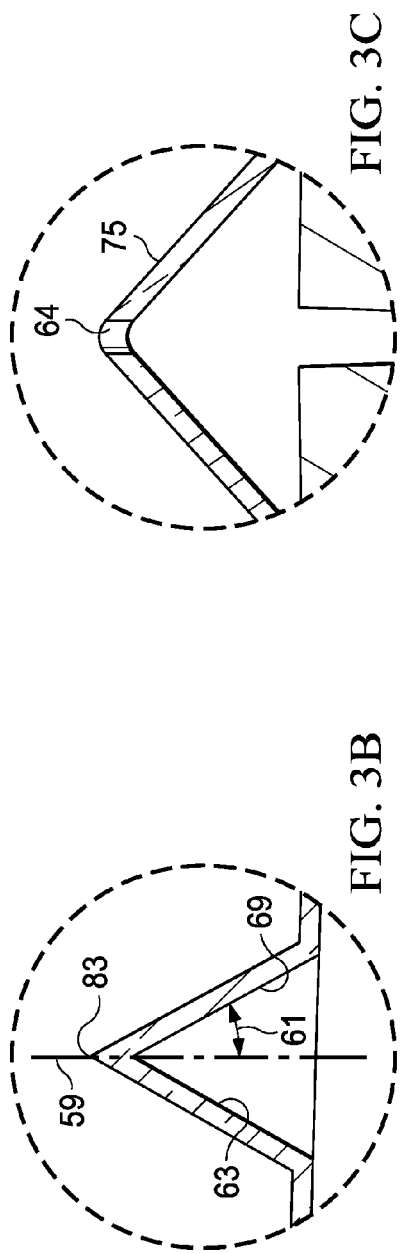
FIG. 3A
FIG. 3B
FIG. 3C

SEE-THROUGH, REDUCED-PRESSURE DRESSINGS AND SYSTEMS

RELATED APPLICATIONS

The present invention claims the benefit, under 35 U.S.C. §119(e), of the filing of U.S. Provisional Patent Application Ser. No. 61/057,807, entitled "Reduced-Pressure Surgical Wound Treatment System," filed May 30, 2008; U.S. Provisional Patent Application Ser. No. 61/057,798, entitled "Dressing Assembly For Subcutaneous Wound Treatment Using Reduce Pressure," filed May 30, 2008; U.S. Provisional Patent Application Ser. No. 61/057,808, entitled "See-Through, Reduced-Pressure Dressing," filed May 30, 2008; U.S. Provisional Patent Application Ser. No. 61/057,802, entitled "Reduced-Pressure Dressing Assembly For use in Applying a Closing Force," filed May 30, 2008; U.S. Provisional Patent Application Ser. No. 61/057,803, entitled "Reduced-Pressure, Linear-Wound Treatment System," filed May 30, 2008; U.S. Provisional Patent Application Ser. No. 61/057,800, entitled "Reduced-Pressure, Compression System and Apparatus for use on a Curved Body Part," filed May 30, 2008; U.S. Provisional Patent Application Ser. No. 61/057,797, entitled "Reduced-Pressure, Compression System and Apparatus for use on Breast Tissue," filed May 30, 2008; U.S. Provisional Patent Application Ser. No. 61/057,805, entitled "Super-Absorbent, Reduced-Pressure Wound Dressing and System," filed May 30, 2008; U.S. Provisional Patent Application Ser. No. 61/057,810, entitled "Reduced-Pressure, Compression System and Apparatus for Use on a Joint," filed May 30, 2008; U.S. Provisional Patent Application Ser. No. 61/121,362, entitled "Reduced-Pressure Wound Treatment System Employing an Anisotropic Drape," filed Dec. 10, 2008; and U.S. Provisional Patent Application Ser. No. 61/144,067, entitled "Reduced-Pressure, Compression System and Apparatus for use on a Joint," filed Jan. 12, 2009. All of these provisional applications are incorporated herein by reference for all purposes.

BACKGROUND

The present invention relates generally to medical treatment systems, and more particularly, to reduced-pressure wound treatment systems suitable for use with linear wounds, such as surgical wounds.

Physicians perform millions of surgical procedures each year around the world. Many of the procedures are performed as open surgery and an increasing number are performed using minimally invasive surgery, such as arthroscopic, laparoscopic, and endoscopic procedures. As one example, the American Society for Aesthetic Plastic Surgery reports that there were more than 450,000 liposuction procedures in the United States in 2007.

Surgical procedures involve acute wounds, e.g., an incision or linear wound, in the skin and related tissue. In addition to surgical wounds, linear wounds are also caused by trauma. In many instances, the linear wound is closed using a mechanical apparatus, such as staples, suture, or adhesives, and then the wound is merely covered with a dry, sterile bandage. Often the bandage must be removed to view the wound to monitor the wound's progress and to check for infection or other issues. Unless otherwise indicated, as used herein, "or" does not require mutual exclusivity.

BRIEF SUMMARY

Shortcomings with certain aspects of wound care are addressed by the illustrative embodiments herein. The present invention may be used on a linear wound, an area wound, or other wound. "Linear wound" refers generally to a laceration or incision whether in a line or not. According to an illustrative embodiment, a see-through dressing assembly for use with a reduced-pressure system for treating a linear wound on a patient includes a closing dressing bolster for providing a closing force when under reduced pressure and a sealing member for covering the closing dressing bolster and providing a seal over the closing dressing bolster. The closing dressing bolster and sealing member are formed from see-through materials sufficient to allow perception of color from a point external to the see-through dressing assembly. The closing dressing bolster may include a top wall and a bottom wall. The top wall and bottom wall are coupled in a spaced relationship. The bottom wall includes a center portion, a first lateral portion, and a second lateral portion. A first closing member is formed on the first lateral portion, and a second closing member is formed on the second lateral portion. When placed under reduced pressure, the first closing member and the second closing member move towards each other.

According to another illustrative embodiment, a system for treating a wound on a patient with reduced pressure allows visual observation of the wound during treatment is presented. The system includes a see-through dressing bolster for placing on the patient's epidermis over the wound; a see-through sealing subsystem for providing a fluid seal over the closing bolster; and a reduced-pressure subsystem for delivering reduced pressure to the sealing subsystem. The sealing subsystem and reduced-pressure subsystem are operable to deliver reduced pressure to the see-through dressing bolster whereupon the system develops a directed force realized at the wound and delivers reduced pressure to the wound. The see-through members are operable to allow light to pass such that the color, shades of color, or a wound edge of the wound may be perceived from a place external to the system.

According to another illustrative embodiment, a method of manufacturing a see-through dressing assembly includes the steps of forming a bolster for providing a directed force to a wound treatment area when under reduced pressure and providing a see-through sealing member to cover the bolster and which allows a fluid seal over the bolster and a patient's epidermis. The step of forming a bolster includes forming a bolster from a see-through material.

According to another illustrative embodiment, a dressing assembly for use with a reduced-pressure treatment system on a patient includes a bolster for placing over a wound on the patient and for providing a directed force when under reduced pressure; a sealing member for covering the bolster and providing a fluid seal over the bolster and a portion of the patient's epidermis; and a visual inspection device for visually detecting the color of the wound on the patient. Still other illustrative embodiments are presented further below.

Other features and advantages of the illustrative embodiments will become apparent with reference to the drawings and detailed description that follow.

BRIEF DESCRIPTION OF THE DRAWINGS

A more complete understanding of the method and apparatus of the present invention may be obtained by reference to the following Detailed Description when taken in conjunction with the accompanying Drawings wherein:

FIG. 3A is a schematic cross-section of an illustrative embodiment of a system for treating a linear wound on a patient;

FIG. 3B is a schematic cross-section of a detail from FIG. 3A;

FIG. 3C is a schematic cross-section of a detail from FIG. 3A;

DETAILED DESCRIPTION OF THE PREFERRED EMBODIMENT

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

Figure 1:
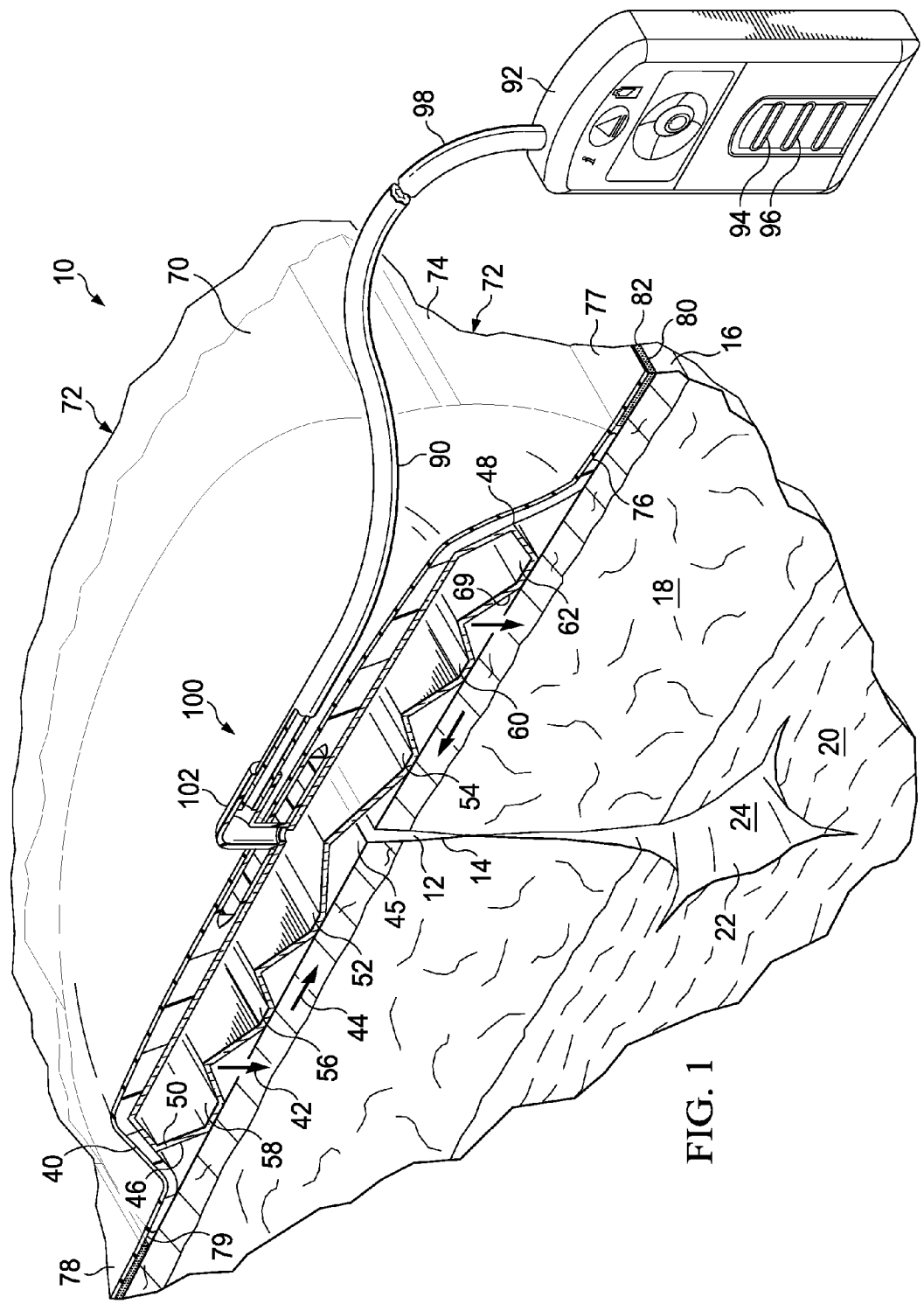
FIG. 1 is a schematic, perspective view, with a portion in cross section, of an illustrative embodiment of a system for treating a linear wound on a patient.
Figure 2:
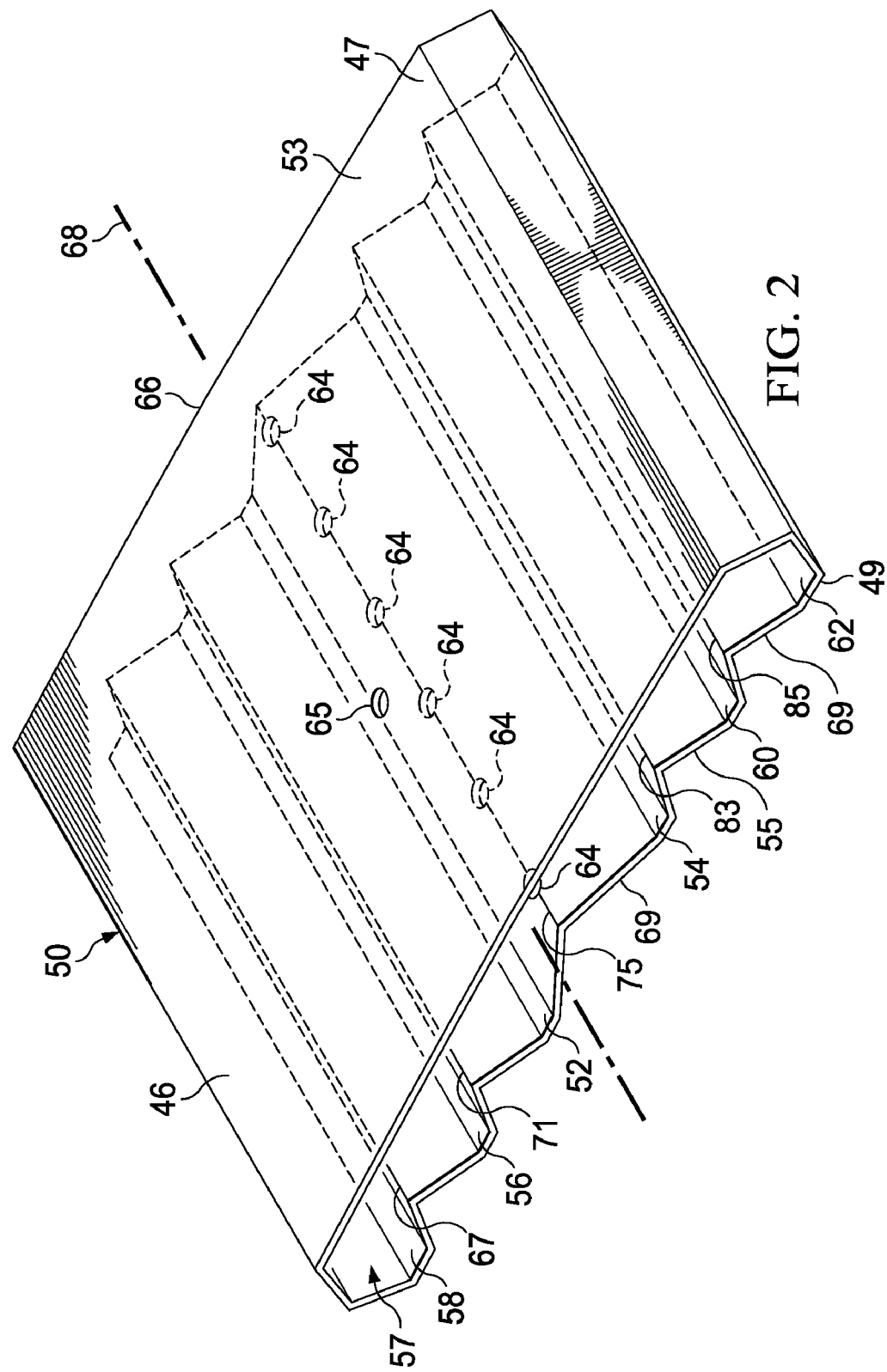
FIG. 2 is a schematic, perspective view of an illustrative embodiment of a closing dressing bolster for use in treating a linear wound on a patient.

Referring to FIGS. 1-3, an illustrative embodiment of a reduced-pressure system 10 for treating a linear wound 12, such as a laceration or, more typically, an incision 14 is presented. The reduced-pressure system 10 may hold or support peri-incisional tissue, enhance tensile strength of the incision 14; compress subcutaneous tissue 20; remove interstitial fluid, which may help reduce or eliminate edema; and isolate the linear wound 12 from infectious sources. The reduced-pressure system 10 may be particularly well suited for use with at-risk patients, e.g., obese patients, diabetic patients, smokers, etc.

While the linear wound 12 may extend to different depths, in this example the incision 14 extends through epidermis 16, dermis 18, and into the subcutaneous tissue 20. An damaged subcutaneous tissue 22 includes, in this illustration, a subcutaneous void 24 or dead space. While not shown in this embodiment, the linear wound 12 may have any number of closing devices employed on the linear wound, e.g., mechanical closing devices (suture, staples, clamps, etc.), adhesives, bonding, etc. The wound may be or include a graft.

The reduced-pressure system 10 may include a dressing assembly 40, which may be placed over the linear wound 12 and used with reduced pressure to supply a directed force, which may include a compressive force 42 or a closing force 44 (or an inward force with respect to an outer edge of the dressing assembly). The dressing assembly 40 may include a closing dressing bolster 46 that under reduced pressure develops the directed force, e.g., the compressive forces 42 or the closing forces 44. The closing dressing bolster 46 may be formed with a bolster body 50. The closing dressing bolster 46 is preferably made from a material that allows flexing and yet is rigid enough to deliver a closing force.

The bolster body 50 may include a first closing member 52 and a second closing member 54. Additional closing members, such as members 56, 58, 60, and 62 may be included. A sealing subsystem 70 and a reduced-pressure subsystem 90 cooperate with the closing dressing bolster 46 to develop the directed force, e.g., the closing force 44 or the compressive force 42.

The closing dressing bolster 46 may be made from a material that helps to distribute reduced pressure to the linear wound 12, provides the compressive force 42, and, through the closing members, e.g., closing member 56, provides a closing force 44—preferably a force that is substantially within the plane of the epidermis 16. In addition, the material for the closing dressing bolster 46 is preferably translucent or see through to an extent that light may pass through allowing one to view the linear wound 12 through the bolster material from a point external to the reduced-pressure system 10. The material from which the closing dressing bolster 46 may be formed is further described below.

As previously noted, the reduced-pressure system 10 may allow wound color, shades of color, wound edge, or other features to be perceived visually from a point external the reduced-pressure system 10. As such, the color, shades of color, nature of the wound edge, or other features may be determined by a healthcare provider without requiring removal of the dressing assembly 40 and thereby may avoid the increased risk of complications and pain of a dressing change. As such, the expense of another a dressing assembly 40 or part of thereof may also be avoided. The reduced-pressure system 10 may also provide the compressive force 42 to the linear wound 12 and that force may help the linear wound 12, subcutaneous tissue 22, or subcutaneous void 24 to heal and may stabilize the linear wound 12 against shear. The reduced-pressure system 10 may also help remove exudates from the linear wound 12 and may help close the void 24.

The sealing subsystem 70 may include the sealing member 72. The sealing member 72 has a first side 74 and a second, inward-facing side 76. A portion of the sealing member 72 may extend beyond the closing dressing bolster 46, e.g., beyond edge 48, to form a flap, or a drape extension 77, which has a first side 78 and a second, inward-facing side 79. The sealing member 72 may be any material that provides a fluid seal that allows reduced pressure to be held. The sealing member may, for example, be an impermeable or semi-permeable, elastomeric material. "Elastomeric" means having the properties of an elastomer. It generally refers to a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Specific examples of sealing member materials include a silicone drape, 3M Tegaderm® drape, acrylic drape (such as one available from Avery Dennison), or an incise drape.

A sealing apparatus 80, or attachment device, may be used to help provide a fluid seal between the drape extension 77 and the patient's epidermis 16. In the present embodiment, the sealing apparatus 80 may be an adhesive 82 that is applied to the second, inward-facing side 79 of the flap extension 77 to provide such a seal against the epidermis 16. The sealing apparatus 80 may be used to hold the sealing member 72 against the patient's epidermis 16 or another layer, such as a gasket or additional sealing member. The sealing apparatus 80 may take numerous forms. For example, the sealing apparatus 80 may be a medically acceptable, pressure-sensitive adhesive that extends about a periphery of the sealing member 72.

The reduced-pressure subsystem 90 includes a reduced-pressure source 92, or therapy unit. The reduced-pressure source 92 provides reduced pressure. The reduced-pressure source 92 may be any device for supplying reduced pressure, such as a vacuum pump, wall suction, or other source. While the amount and nature of reduced pressure applied to a tissue will typically vary according to the application, reduced pressure will typically be between −5 mm Hg and −500 mm Hg and more typically between −100 mm Hg and −300 mm Hg. In one embodiment, the reduced pressure is held around −200 mm Hg. The reduced-pressure source 92, for convenience and mobility purposes, may be a battery-operated unit that is capable of providing a continuous and intermittent reduced pressure. The reduced-pressure source 92, or therapy unit, may include a canister 94, or reservoir, and may be provided with windows 96 to allow the patient or healthcare provider to view the fill status of the canister 94. The reduced-pressure subsystem 90 further includes a reduced-pressure delivery conduit 98, or medical tubing, which if fluidly coupled to a reduced-pressure interface 100, such as a port 102. The reduced-pressure delivery conduit 98 and the reduced-pressure interface 100 allow reduced pressure to be delivered into the sealing subsystem 70.

As used herein, "reduced pressure" generally refers to a pressure less than the ambient pressure at a linear wound 12, tissue site, or treatment site that is being subjected to treatment. In most cases, this reduced pressure will be less than the atmospheric pressure at which the patient is located. Alternatively, reduced pressure may be less than a hydrostatic pressure at the tissue site. Unless otherwise indicated, values of pressure stated herein are gauge pressures. Reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure.

The closing dressing bolster 46 may be made from a polymer and is preferably a soft polymer. In one illustrative embodiment, the closing dressing bolster 46 is a material having a durometer of 50 Shore A, but other materials and characteristics are possible. The closing dressing bolster 46 and the bolster body 50 may be made of a see-through material, as is a sealing member 72, in order to allow the color, shades of color, wound edges, or other features of the linear wound 12 to be viewed from a point external to the reduced-pressure system 10 (see FIG. 6). A color change, or change in the shade of a color, of the linear wound 12 can signify the onset of infection or other issues, and such visual cues provide useful information to the healthcare provider. The bolster body 50 may be made from a flexible closing bolster material, e.g., a soft polymer, a medical grade silicone, or other suitable material. The closing dressing bolster 46 may be extruded, pour molded, injection molded, blow molded, or formed by other manufacturing techniques. "Flexible" means able to move enough to generate the inward closing force.

Referring now primarily to FIG. 2, the closing dressing bolster 46 is shown with a plurality of apertures 64 formed on a second, inward-facing side or surface 49 of a second wall 55, or bottom wall, of the bolster body 50. The apertures 64 are formed under a center portion 66, and in particular, near center line 68 of the bolster body 50. A detail showing one aperture 64 is shown in FIG. 3C. A first wall 53, or top wall, and the second wall 55 are coupled in a spaced relationship to form a hollow region or central compartment 57. Referring again primarily to FIG. 2, the apertures 64 facilitate the transmission of reduced pressure by the bolster body 50 to the linear wound 12. Additional apertures in various patterns may be provided in the bolster body 50 to facilitate communication of reduced pressure to the patient's epidermis 16, and, in particular, to the linear wound 12. One or more apertures, such as aperture 65, may be formed on a first side 47 of the first wall 53 of the bolster body 50. Closing members 52, 54, 56, 58, 60, and 62 are shown on the second, inward-facing side 49. Closing members 52, 56, and 58 are on a first lateral side of the center portion 66 and closing members 54, 60, and 62 are on a second lateral side of the center portion 66.

As shown clearly in FIGS. 3A and 3B, an oblique surface 69 has an angle formed with respect to an imaginary plane extending vertically (vertical for the orientation shown in FIG. 2). The oblique surface 69, which is opposite a surface 63, is shown making an angle 61 with respect to a reference vertical plane 59 formed at the apex of the oblique surface 69.

In operation, when treatment is desired, the closing dressing bolster 46 is placed over the linear wound 12 with the center portion 66 over the linear wound 12 proximate a center wound area 45. If the closing dressing bolster 46 is not pre-manufactured with the sealing member 72 applied on the first side 47, then the sealing member 72 is applied over the first side 47 of the closing dressing bolster 46 and beyond the closing dressing bolster 46 to form the flap extension or drape extension 77. The drape extension 77 is either taped down or an adhesive 82 is applied to provide a fluid seal between the sealing member 72 and the patient's epidermis 16. "Fluid seal," or "seal," means a seal adequate to hold reduced pressure at the desired site given the particular reduced-pressure subsystem involved.

The reduced-pressure subsystem 90 is fluidly coupled to the sealing subsystem 70 through the reduced-pressure interface 100. The reduced-pressure source 92 is activated and develops and delivers reduced pressure through the reduced-pressure delivery conduit 98 to the reduced-pressure interface 100. When activated, the reduced-pressure source 92 delivers reduced pressure to the sealing subsystem 70 and reduced pressure causes the closing dressing bolster 46 to develop the compressive force 42. The geometry of the closing dressing bolster 46 may cause a bending moment to develop about the center portion 66 and thereby cause the closing members 52, 54, 56, 58, 60, and 62 to develop a resultant force downward and inward (for the orientation shown). This action produces the directed force, e.g., the compressive force 42 or the closing force 44. These forces may be experienced at or near the linear wound 12.

Referring primarily to FIG. 2, the development of the closing force or compressive force is described in more detail. Each of the oblique surfaces 69 between adjacent closing members, 58 and 56, 56 and 52, 52 and 54, 54 and 60, and 60 and 62, form part of a triangle-shaped ridge, each having an apex: first apex 67, second apex 71, central apex 75, third apex 83, and fourth apex 85. As the reduced pressure enters the aperture 65, the central compartment 57 is evacuated until some or all of the apexes 67, 71, 75, 83, and 85 encounter the first wall 53. Reduced pressure is also delivered from the central compartment 57 through apertures 64 and may provide a force urging the apexes higher, or trying to make the angle associated with each apex smaller. As a result of one or more of these actions, the closing members 52, 54, 56, 58, 60, and 62 are urged toward the center line 68 and, through friction against the patient's epidermis from the closing members 52, 54, 56, 58, 60, and 62, the closing force is developed on the patient's epidermis. The compressive force may be developed as the first wall 53 and second wall 55 are pulled by reduced pressure toward the patient or in the direction going from the first wall 53 to the second wall 55.

Referring now primarily to FIGS. 4A, 4B, 4C, and 4D, another illustrative embodiment of a closing dressing bolster 146 is presented. The closing dressing bolster 146 has a bolster body 150 formed with a first closing member 152 and a second closing member 154. A third closing member 156 and a fourth closing member 158 are also shown. The closing members 152 and 156 are formed on a first side or first portion 153 which is one side of a center plane 168, or center portion, and may extend the longitudinal length of the closing dressing bolster 146. The closing members 154 and 158 are formed on a second portion or side 155, which is on the other side of the center plane 168.

A central trough area 157 may help the bolster body 150 to flex in that region as a bending moment is developed under reduced pressure. The bending moment helps to press the closing members 152, 154, 156, and 158 into the patient's epidermis and may provide the directed force, e.g., the compressive force and closing force directed towards the central wound area (e.g., area 45 in FIG. 1). The shape of the bolster body 150 in this illustrative embodiment has been chosen for strength and ease in extruding from a material, e.g., silicone, and so that the bolster body 150 collapses or moves in a desired way to develop the directed force, e.g., the compressive or closing forces. The closing dressing bolster 146 may be made of a see-through or at least partially transparent material so that the closing dressing bolster 146 may help the color, shades of color, wound edge, or other features of the linear wound underneath the closing dressing bolster 146 be viewed from a point exterior to a system utilizing the closing dressing bolster 146.

Figure 4A:
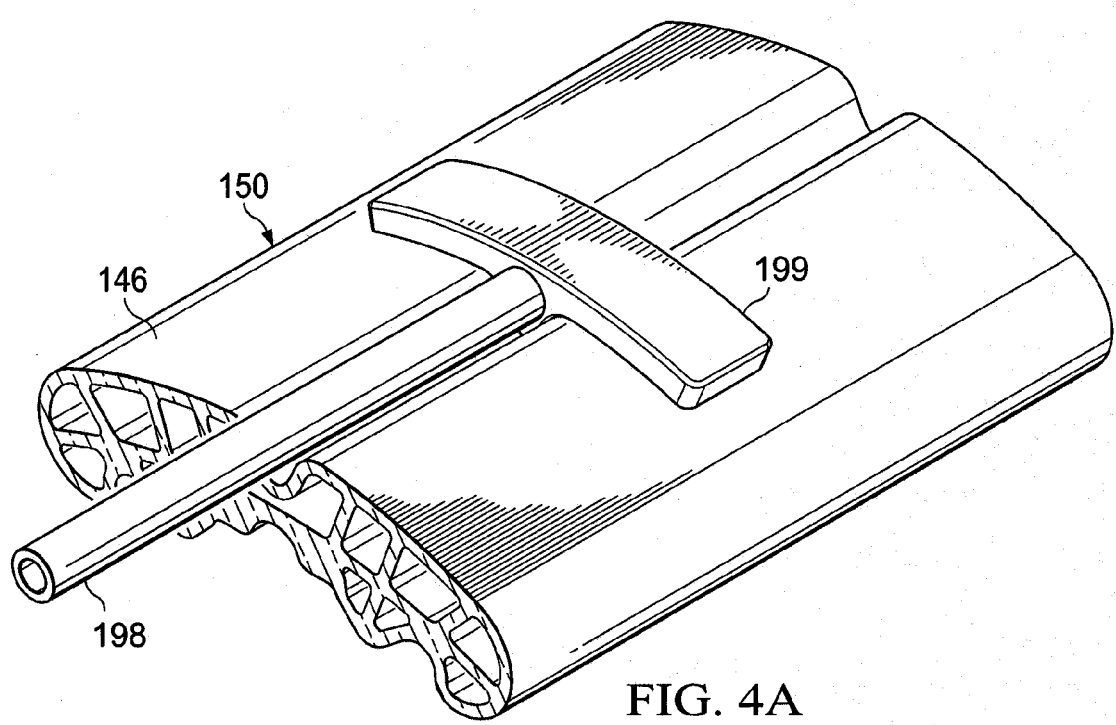
FIG. 4A is a schematic, perspective view of an illustrative embodiment of a closing dressing bolster for use in treating a linear wound on a patient.
Figure 4B:
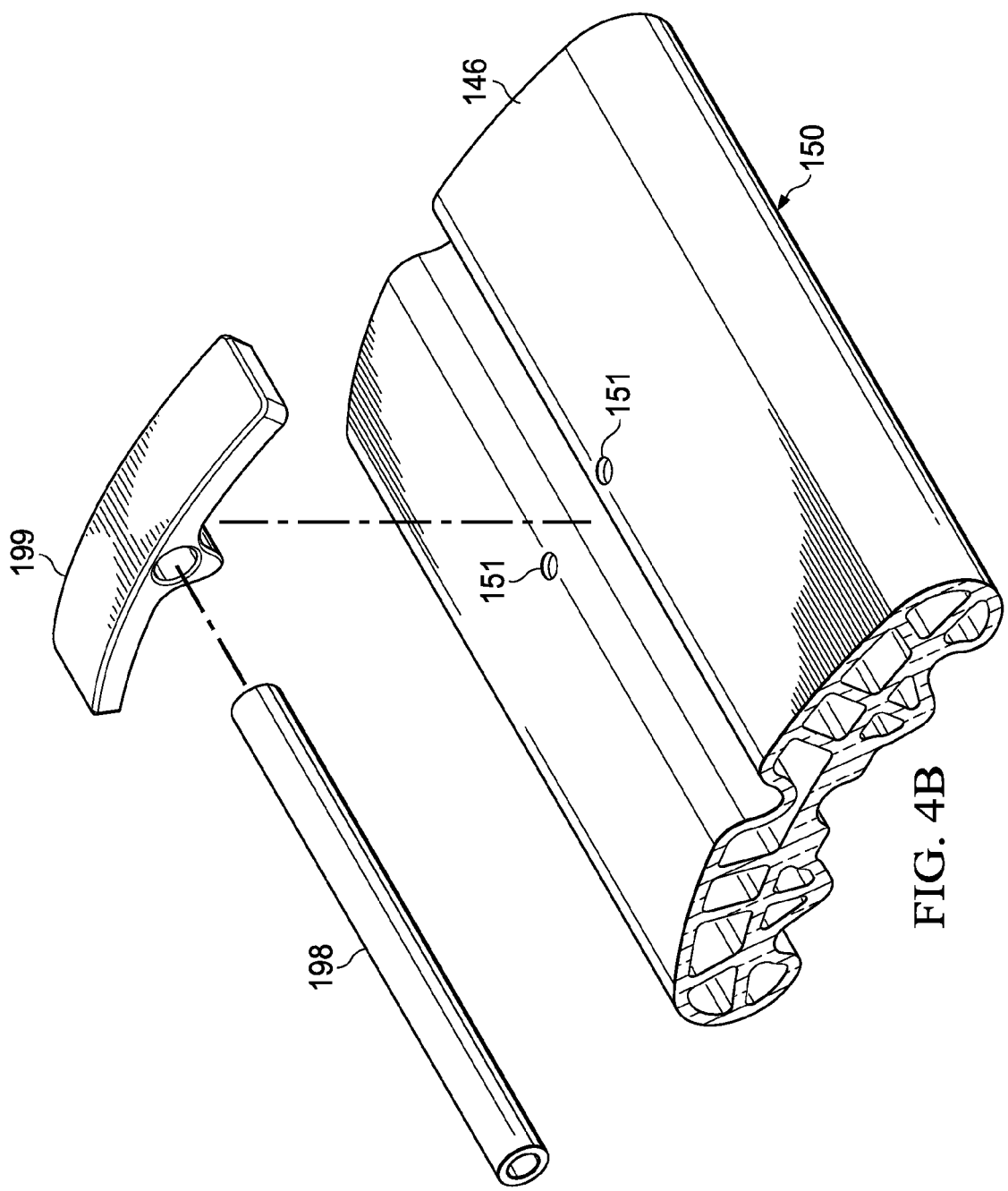
FIG. 4B is a partially exploded, perspective view of the closing dressing bolster of FIG. 4A showing one illustrative embodiment of a tubing connector.

As shown in FIGS. 4A and 4B, a tubing connector 199 may be used to provide reduced pressure to the closing dressing bolster. The tubing connector 199 is sized and configured to mate with central trough area 157 on the closing dressing bolster 146. The tubing connector 199 is fluidly coupled to a reduced-pressure delivery conduit 198 whereby reduced pressure is delivered to the closing dressing bolster 146. Apertures 151 allow reduced pressure to communicate inside the closing dressing bolster 146. As shown clearly in FIG. 4C, an aperture 164 may be formed in a portion of the closing dressing bolster 146 to help communicate reduced pressure to the linear wound below.

Figure 4C:
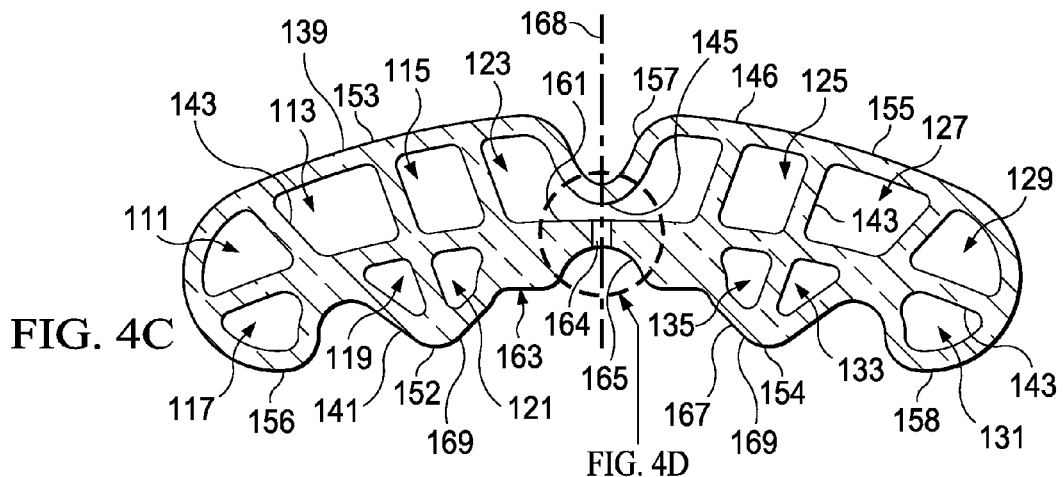
FIG. 4C is a cross-section of the closing dressing bolster of FIG. 4A.
Figure 4D:
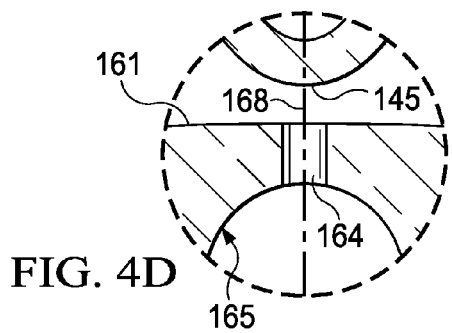
FIG. 4D is a detail of the closing dressing bolster of FIG. 4C.

Referring now primarily to FIGS. 4C-4D, the development of the closing force or a compressive force will be described in more detail. In this illustrative embodiment, the bolster body 150 has been extruded with a central compartment 123 and a plurality of compartments. Six of the plurality of compartments 111, 113, 115, 117, 119, and 121 are formed on the first portion 153. The central compartment 123 is formed substantially adjacent to the central trough 157. Six of the plurality of compartments 125, 127, 129, 131, 133, and 135 are formed on the second portion 155. In this embodiment, only the central compartment 123 receives reduced pressure and does so through apertures 151.

The plurality of compartments, e.g., compartments 111, 113, 115, 117, 119, 121, 125, 127, 129, 131, 133, and 135 are formed using a first wall 139 (or top wall), a second wall 141 (or bottom wall), and a plurality of web members 143. The plurality of compartments provides strength to keep the first wall 139 from collapsing against the second wall 141, except that a lower portion 145 of the central trough 157 is designed to collapse under reduced pressure against a shelf portion 161 of the central compartment 123. It should be noted that first closing member 152 and second closing member 154 are spaced apart and sized and configured to provide a treatment trough 163. The treatment trough 163 may have a dome-cutout 165 and oblique walls 167. The first closing member 152 is formed on a first lateral portion with respect to the center plane 168, and the second closing member 154 is formed on a second lateral portion with respect to the center plane 168.

As reduced pressure is delivered to apertures 151, the reduced pressure enters the central compartment 123 and is delivered through aperture 164 into the treatment trough 163. The reduced pressure causes the lower portion 145 of the central trough 157 to collapse and touch the shelf portion 161 of the central compartment 123. In addition, reduced pressure in the treatment trough 163 pulls the oblique walls 169 towards each other. One or more of these actions causes the bolster body 150 to flex, or bend, about the center plane 168 and thereby urges the closing members towards the center plane 168. The plurality of compartments preferably do not collapse and continue to provide strength. Moreover, as the reduced pressure pulls the closing dressing bolster 146 inward, i.e., in the direction going from the first wall 139 to the second wall 141, and a compressive force is developed.

Figure 5:
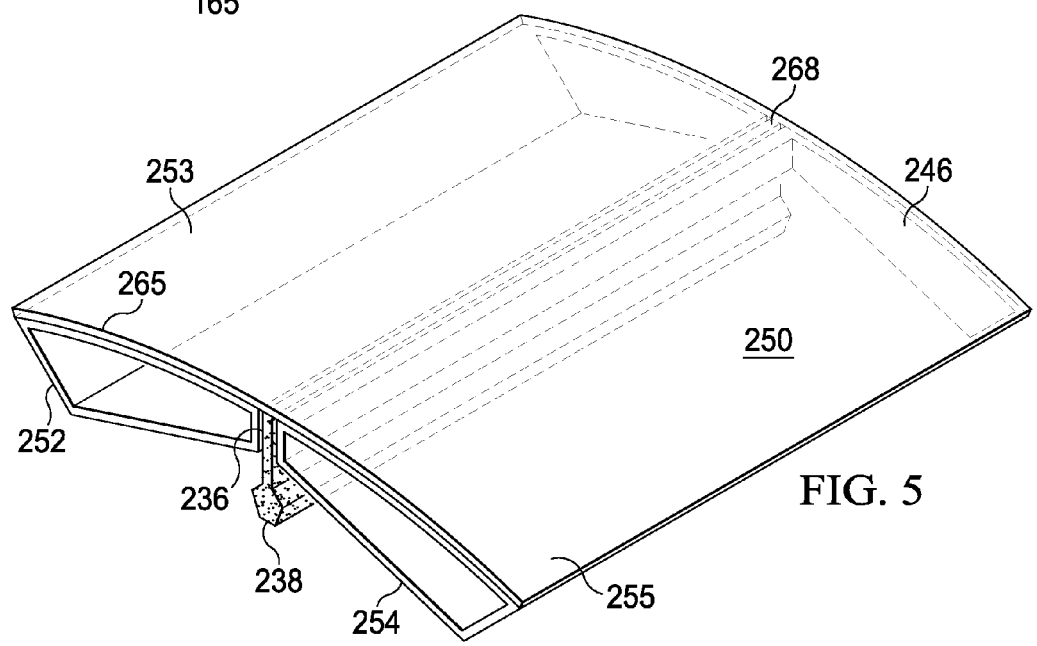
FIG. 5 is a schematic, perspective view of an illustrative embodiment of a closing dressing bolster for use in treating a linear wound on a patient.

Referring now primarily to FIG. 5, another embodiment of a closing dressing bolster 246 is presented. The closing dressing bolster 246 includes a bolster body 250 formed with a first closing member 252 on a first side 253, or first lateral side, and a second closing member 254 on a second side 255, or second lateral side. The first and second closing members 252 and 254 have oblique walls that angle up (for orientation shown) toward the wicking material holder 236. With respect to a center portion 268, an overlay piece 265, or overlay, may cover and hold the closing members 252 and 254. A gap between closing members 252 and 254 forms a wicking-material holder 236 that holds a wicking material 238. The shape of the wicking material 238 and the substance of the wicking material 238 may be operable to help keep an underlying linear wound (e.g., linear wound 12 in FIG. 1) dry and clean.

The materials that may be used for the wicking material 238 include hydrophobic materials, hydrophilic materials, and all the materials listed elsewhere that may be used for a shaped dressing bolster 532 described below (see FIG. 8).

The overlay piece 265 and closing members 252 and 254 may be made of a see-through material that allows the closing dressing bolster 246 to be used with a system that allows a healthcare provider to view the color, shades of color, wound edges, or other features of the linear wound beneath the closing dressing bolster 246 from a point external to the closing dressing bolster 246 (see FIG. 6 for an example) and external to the system.

In operation, the closing dressing bolster 246 may develop a bending moment under reduced pressure causing the lower portion of the first closing member 252 and the lower portion of the second closing member 254 to press downward (for the orientation shown) and inward on the patient's epidermis causing both a compressive force or a closing force towards the linear wound. Reduced pressure delivered to the wicking-material holder 236 may move the first closing member 252 and the second closing member 254 closer together and thereby provide the closing force. The closing dressing bolster 246 is sized and configured so that the wicking material 238 may be in contact with the linear wound and thereby helps to remove any fluids that might have emanated from the linear wound. Any such fluids would be delivered to a reduced-pressure interface and then be delivered by a reduced-pressure conduit to a canister under the influence of a reduced-pressure source.

Figure 6:
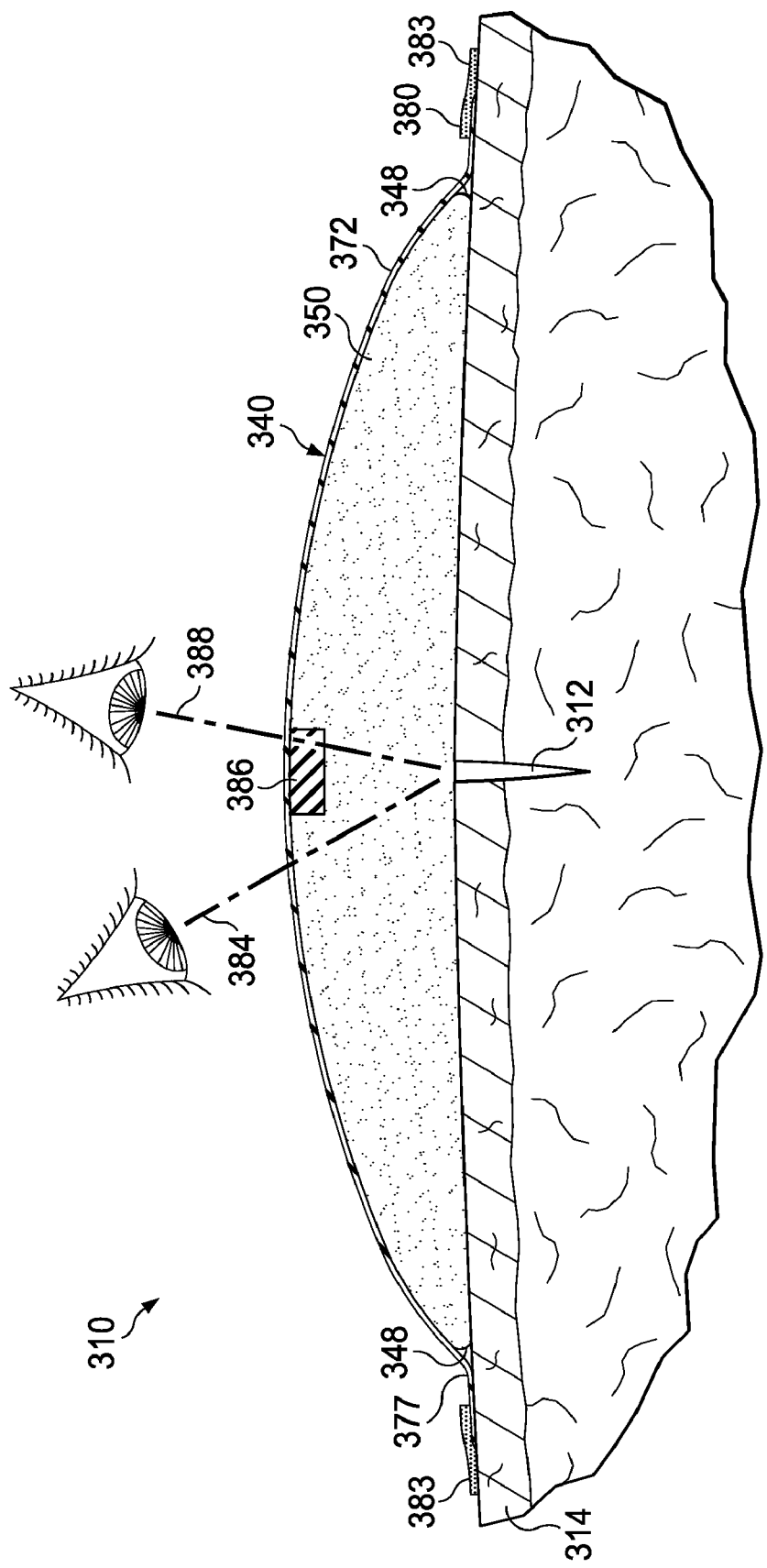
FIG. 6 is a schematic cross-section of a portion of an illustrative embodiment of a system for treating a linear wound on a patient.

The illustrative closing dressing bolsters 46, 146, and 246 presented above may provide for the visual determination of the color, shades of color, wound edge, or other features of the wound from a location external to the closing dressing bolster. This feature is also possible with other types of dressings as will now be discussed. Referring now to FIG. 6, a portion of a reduced-pressure treatment system 310 is shown. The reduced-pressure treatment system 310 includes a see-through dressing assembly 340, which has a bolster body 350. The bolster body 350 may be made of any number of materials, such as a bolster mesh or bolster foam, provided that the spacing of pores on the foam (non-opaque foam) or between structural elements of the material allow for sufficient light to pass through the material such that the color, shades of color, wound edge, or other features of a linear wound 312 can be seen from a point external to the reduced-pressure treatment system 310, e.g., can be seen in a line of sight location shown by reference numeral 384. For example, the bolster body 350 may be formed from silicone or porous foam, e.g., a Granu-Foam® material available from Kinetic Concepts, Inc. of San Antonio, Tex. The pore size and density may be varied to help provide the see-through characteristic.

In an alternative illustrative embodiment, a window 386, such as a window made of see-through silicone, may be placed over a portion of the bolster material such that when reduced pressure is provided to the bolster body 350 and the window 386 is compressed down further on the bolster material, the linear wound 312 becomes visible through the window 386 from a point exterior to the bolster body 350 and the system 310. For example, a patient or healthcare provider may see the linear wound 312 on a line of sight 388.

In another alternative, illustrative embodiment, clear beads may be used as or included within bolster body 350. The beads may be arranged within the bolster body so that under negative pressure, the beads come together over the wound allowing the patient or healthcare provider to see through to the wound from a point exterior or external to the bolster body 350 and the system 310. The bolster body 350 may be a mesh material that the beads can displace as they come together under reduced pressure.

In another embodiment, a window can be made such that when reduced pressure is removed from the bolster body 350, a biased portion moves aside allowing one to view the linear wound 312. For example, two portions of the bolster body 350 may overlap as reduced pressure compresses the two portions, but when reduced pressure is removed, the portions separate and allow a clear view of the linear wound. As such, it will be appreciated that numerous visual inspection devices may be used to allow the color and other characteristics of the wound to be visually detected. The visual inspection device may be a see-through bolster and a see-through sealing member, a window 386, a bolster material that allows adequate light to pass, a plurality of clear beads, or a moveable portion of a bolster that allows visual inspection when not under reduced pressure.

The bolster body 350 is shown covered by a sealing member 372 that extends beyond the bolster body 350, e.g., beyond edge 348, to form a drape extension 377. The drape extension 377 may be sealed to form a fluid seal between the sealing member 372 and a patient's epidermis 314 using a sealing apparatus 380, such as a drape tape 383 or other sealing device.

Figure 7:
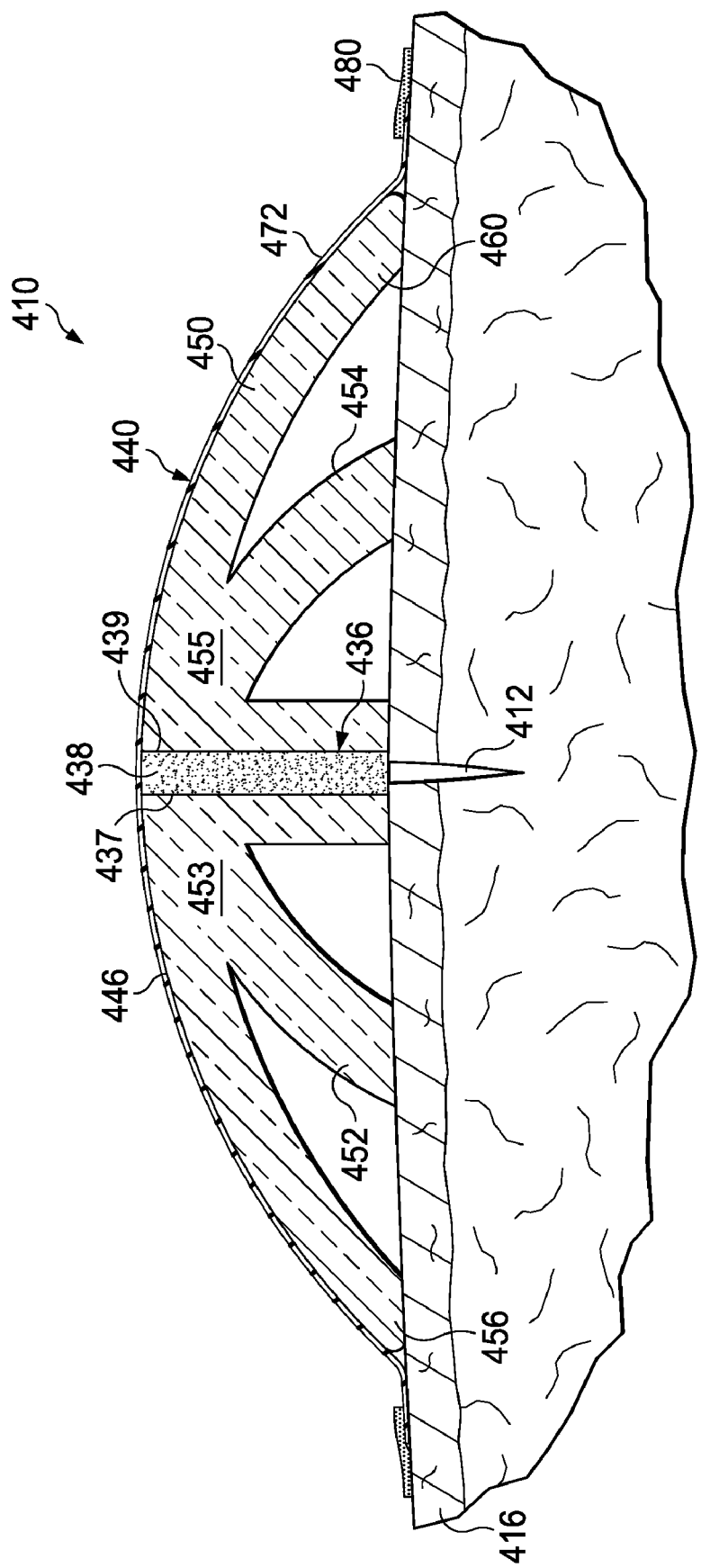
FIG. 7 is a schematic cross-section of an illustrative embodiment of a portion of a system for treating a linear wound on a patient.

Referring now primarily to FIG. 7, a portion of an illustrative system 410 for treating a linear wound 412 is presented. The system 410 includes a dressing assembly 440. The dressing assembly 440 includes a dressing bolster 446, which has a dressing body 450. The dressing body 450 may be formed with two portions: the first side, or first lateral portion 453, and a second side, or second lateral portion 455. The first portion 453 and second portion 455 may be integrally connected or may be two separate pieces. The first portion 453 is formed with closing members 452 and 456. The second portion 455 is formed with closing members 454 and 460. Under reduced pressure, the closing members 452, 454, 456, and 460 develop both a compressive force and a closing force towards the linear wound 412. The dressing body 450 is shown covered by a sealing member 472 that is sealed with a sealing apparatus 480 to provide a seal against a patient's epidermis 416.

A first wall 437 on the first portion 453 and a second wall 439 on the second portion 455 together may form a wicking-material holder 436 for holding a wicking material 438. The wicking material 438 may be held against the linear wound 412 to help to remove any fluids, e.g., exudates, when the dressing assembly 440 is place under reduced pressure.

Figure 8:
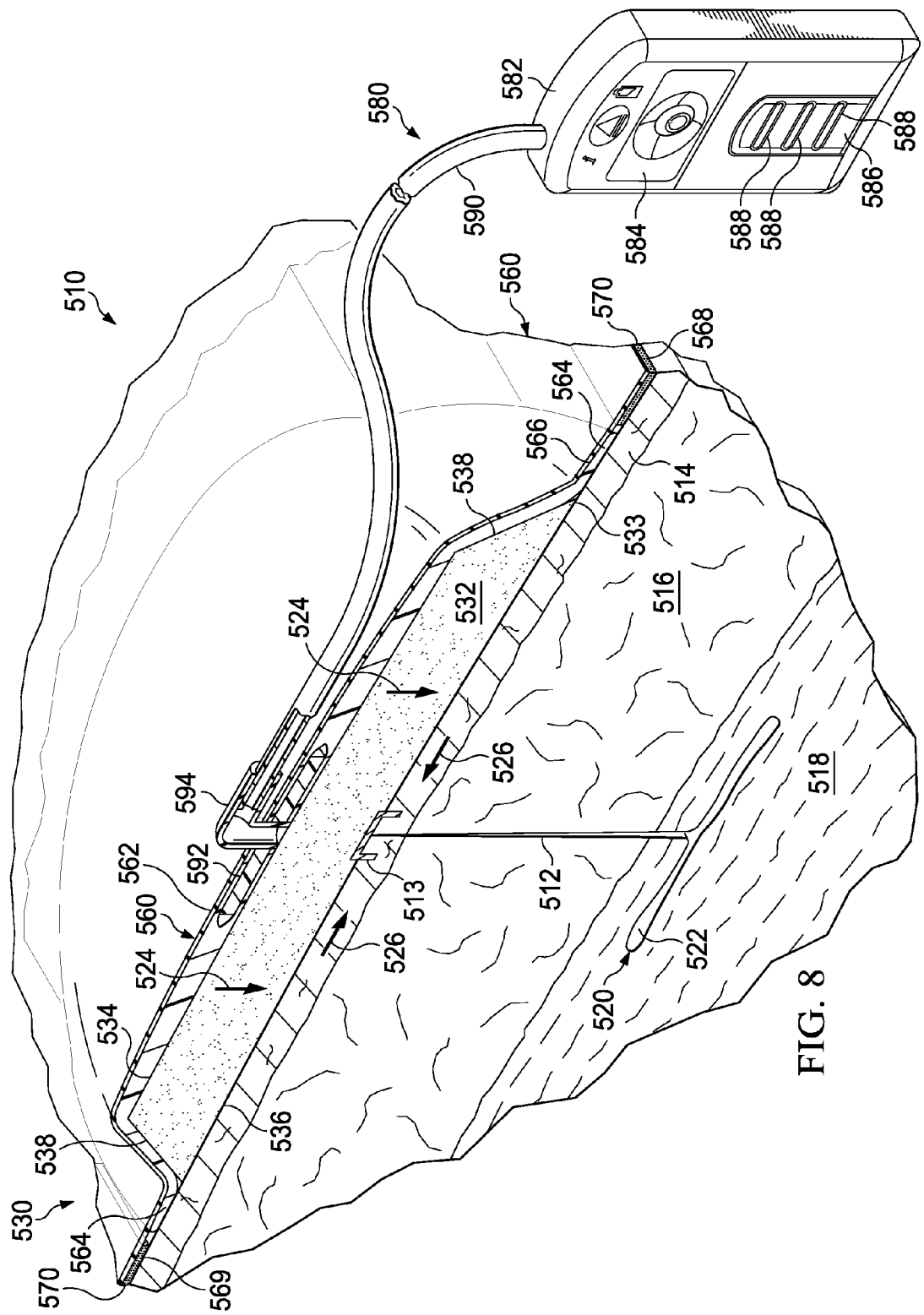
FIG. 8 is a schematic, perspective view, with a portion in cross section, of an illustrative embodiment of a system for treating damaged subcutaneous tissue that allows the wound to be seen from a point external to the system.

Referring now primarily to FIG. 8, an illustrative see-through wound treatment system 510 is presented that allows a healthcare provider to view a treatment site, e.g., linear wound 512, area wound, a portion of intact epidermis 514, etc., and may provide a compressive force. The see-through wound treatment system 510 may provide for the treatment of subcutaneous damaged tissue and may allow the treatment site to be viewed from a place external to the see-through wound treatment system 510.

The see-through wound treatment system 510 is shown in a peri-incisional region around the linear wound 512, which is through the epidermis 514, dermis 516, and reaching into a hypodermis, or subcutaneous tissue 518. The subcutaneous tissue 518 may include numerous tissue types, such as fatty tissue or muscle. A damaged subcutaneous tissue site 520 is shown extending out from the linear wound 512 and includes, in this instance, a subcutaneous defect, dead space, or void 522. The damaged subcutaneous tissue site 520 may be caused by surgical procedures, such as liposuction. The damaged subcutaneous tissue site 520 may include voids, such as the void 522, open spaces, and various defects that can be troublesome for a number of reasons, such as fluid accumulation that may result in edema.

The linear wound 512 may be closed using any closing device or technique, such as staples, sutures, or adhesive, but is shown in this illustrative embodiment with a staple 513. The see-through wound treatment system 510 may be used for treating an area and, in particular, may be used for treating a subcutaneous tissue site 520 and the tissue around subcutaneous tissue site 520, but the see-through wound treatment system 510 may also be used to treat the more limited area of a linear wound 512.

The see-through wound treatment system 510 includes a dressing assembly 530, which includes the shaped dressing bolster 532, a sealing subsystem 560, and a reduced-pressure subsystem 580. In operation, the see-through wound treatment system 510 may develop the directed force, which may include a net compressive force, represented by reference numerals 524, that is realized in the subcutaneous tissue site 520. As described further below, the shaped dressing bolster 532 may be shaped and configured to allow the compressive force 524 to be distributed fairly evenly over the patient's epidermis 514. Otherwise, if there are areas of substantially increased force as compared to other areas on the epidermis 514, skin irritation may result.

The directed force may also include the closing force, or inward force, i.e., a force towards an interior portion of the dressing assembly 530. The closing force is represented by reference numerals 526. The closing force 526 remains substantially within the plane of the epidermis 514. In other words, the closing force 526 operates mainly within the epidermis 514. In addition, the see-through wound treatment system 510 is operable to deliver reduced pressure to the linear wound 512 and, depending on the phase of healing and the nature of the linear wound 512, through the linear wound 512 such that reduced pressure is realized at the level of any subcutaneous voids 522 to help approximate—bring together—the tissues in that region as well as to help remove any air or any other fluids.

The dressing assembly 530 includes the shaped dressing bolster 532 that has a first side 534 and a second, inward-facing side 536. The shaped dressing bolster 532 may be sized and shaped to substantially match the estimated area of the damaged subcutaneous tissue site 520 although a larger or smaller size may be used in different applications. The shaped dressing bolster 532 has an edge 538. The shaped dressing bolster 532 may be made of a number of different medical bolster materials, i.e., materials suitable for use in medical applications and that may be made sterile. In one illustrative embodiment, the shaped dressing bolster 532 is made from a medical bolster material that is a manifold material. In one illustrative embodiment, the shaped dressing bolster 532 is made from bolster material that is a porous and permeable foam-like material and, more particularly, a reticulated, open-cell polyurethane or polyether foam that allows good permeability of wound fluids while under reduced pressure. One such foam material that has been used is the VAC® Granu-Foam® material available from Kinetic Concepts, Inc. (KCI) of San Antonio, Tex. Any material or combination of materials may be used for the bolster material provided that the bolster material is operable to distribute, or manifold, reduced pressure.

The term "manifold" as used herein generally refers to a substance or structure that is provided to assist in applying reduced pressure to, delivering fluids to, or removing fluids from a tissue site. The bolster material may also be a combination or layering of materials; for example, a first bolster layer of hydrophilic foam may be disposed adjacent to a second bolster layer of hydrophobic foam to form the bolster material. The term "fluid" as used herein generally refers to gas or liquid, but may also include any other flowable material, including but not limited to gels, colloids, and foams.

The reticulated pores of the Granufoam® material, which are typically in the range of about 400 to 600 microns, are helpful in carrying out the manifold function, but other materials may be used. The density of the medical bolster material, e.g., Granufoam® material, is typically in the range of about 1.3 lb/ft$^3$-1.6 lb/ft$^3$ (20.8 kg/m$^3$-25.6 kg/m$^3$). A material with a higher density (smaller pore size) than Granufoam® material may be desirable in some situations. For example, the Granufoam® material or similar material with a density greater than 1.6 lb/ft$^3$ (25.6 kg/m$^3$) may be used. As another example, the Granufoam® material or similar material with a density greater than 2.0 lb/ft$^3$ (32 kg/m$^3$) or 5.0 lb/ft$^3$ (80.1 kg/m$^3$) or even more may be used. The more dense the material is, the higher compressive force that may be generated for a given reduced pressure. If a foam with a density less than the tissue at the tissue site is used as the medical bolster material, a lifting force may be developed.

The bolster material may be a reticulated foam that is later felted to thickness of about ⅓ the foam's original thickness. Among the many possible materials, the following may be used: GranuFoam® material or a Foamex® technical foam (www.foamex.com). In some instances it may be desirable to add ionic silver to the bolster material in a microbonding process or to add other substances to the bolster material, such as antimicrobial agents. The bolster material may be isotropic or anisotropic depending on the exact orientation of the directed force that is desired during reduced pressure. The bolster material may be made anisotropic by adding filaments, felting a portion, adding adhesive selectively, etc. The bolster material could be a bio-absorbable material.

The sealing subsystem 560 includes a sealing member 562, or drape, which is analogous to the sealing member 72. The sealing member 562 may be coupled to the shaped dressing bolster 532. For example, the sealing member 562 and shaped dressing bolster 532 may be coupled using adhesives, such as an acrylic adhesive, silicone adhesive, hydrogel, hydrocolloid, etc. As another example, the sealing member 562 and the shaped dressing bolster 532 may be bonded by heat bonding, ultrasonic bonding, and radio frequency bonding, etc. The coupling may occur in patterns or completely. Structure may be added to the bond to make the sealing member 562 behave anisotropically in a desired direction, i.e., to make an anisotropic drape material. An anisotropic drape material helps the dressing assembly 530 to primarily move in a given direction, i.e., only about a certain axis or axes.

In the illustrative embodiment of FIG. 8, the sealing member 562 may be sized to extend beyond the shaped dressing bolster 532, e.g., beyond the edge 538 on an extremity 533, to form a drape extension 564, or extension. The drape extension 564 has a first surface 566 and a second, inward-facing surface 568. The sealing member 562 may be sealed against the epidermis 514 of the patient using a sealing apparatus 569, which helps to provide a seal and allows reduced pressure to be maintained by the reduced-pressure subsystem 580 at the treatment site. The sealing apparatus 569 may take numerous forms, such as an adhesive 570; a sealing tape, or drape tape or strip; double-side drape tape; paste; hydrocolloid; hydrogel; or other sealing device. If a tape is used, the tape may be formed of the same material as the sealing member 562 with a pre-applied, pressure-sensitive adhesive. The pressure sensitive adhesive 570 may be applied on the second, inward-facing surface 568 of the drape extension 564. The pressure-sensitive adhesive 570 provides a seal between the sealing member 562 and the epidermis 514 of the patient. Before the sealing member 562 is secured to the patient, the pressure-sensitive adhesive 570 may have removable strips or backing covering the pressure-sensitive adhesive 570.

The reduced-pressure subsystem 580 includes a reduced-pressure source 582, or therapy unit, which can take many different forms. The reduced-pressure source 582 provides reduced pressure as a part of the see-through wound treatment system 510. The reduced-pressure source 582 may be any device for supplying reduced pressure, such as a vacuum pump, wall suction, or other source. While the amount and nature of reduced pressure applied to a tissue will typically vary according to the application, reduced pressure will typically be between −5 mm Hg and −500 mm Hg and more typically between −100 mm Hg and −300 mm Hg. In order to maximize patient mobility and ease, the reduced-pressure source 582 may be a battery-powered, single-use reduced-pressure generator, which facilitates application in the operating room and provides mobility and convenience for the patient during the rehabilitation phase.

In the illustrative embodiment of FIG. 8, the reduced-pressure source 582 is shown having a battery compartment 584 and a canister region 586 with windows 588 providing a visual indication of the level of fluid within the canister region 586. An interposed membrane filter, such as hydrophobic or oleophobic filter, may be interspersed between a reduced-pressure delivery conduit, or tubing, 590 and the reduced-pressure source 582.

Reduced pressure developed by reduced-pressure source 582 is delivered through the reduced-pressure delivery conduit 590 to a reduced-pressure interface 592, which may be an elbow port 594. In one illustrative embodiment, the elbow port 594 is a TRAC® technology port available from KCI of San Antonio, Tex. The reduced-pressure interface 592 allows reduced pressure to be delivered to the sealing subsystem 560 and realized within an interior portion of the sealing subsystem 560. In this illustrative embodiment, the elbow port 594 extends through the sealing member 562 and into the shaped dressing bolster 532.

In operation, the see-through wound treatment system 510 is applied to the linear wound 512. The see-through wound treatment system 510 may be applied to the linear wound 512 in the operating room after a surgical procedure on the patient. The second, inward-facing side 536 of the shaped dressing bolster 532 is placed against the patient's epidermis 514 with the shaped dressing bolster 532 over the damaged subcutaneous tissue site 520 and with a portion of the shaped dressing bolster 532 over the linear wound 512. The dressing assembly 530 may be sized for the typical application involved in the procedure performed by a healthcare provider. The dressing assembly 530 may be sized, shaped, and configured to work with different anatomical applications, such as the abdomen, chest, arms, thighs, etc.

If the sealing member 562 has not already been coupled, the sealing member 562 is placed over the first side 534 of the shaped dressing bolster 532 with a portion extending beyond the shaped dressing bolster 532 to form the drape extensions 564. The drape extensions 564 may then be taped down or an adhesive 570 used to form a seal between the sealing member 562 and the patient's epidermis 514. The seal need only be adequate to allow the see-through wound treatment system 510 to hold reduced pressure on the desired treatment area. The reduced-pressure interface 592 and the reduced-pressure source 582 are fluidly coupled using the reduced-pressure delivery conduit 590. The reduced-pressure source 582 may then be activated and reduced pressure delivered to the shaped dressing bolster 532.

As the pressure is reduced in the shaped dressing bolster 532, the shaped dressing bolster 532 compresses and contracts laterally and forms a semi-rigid substrate, and a number of beneficial forces and actions may take place. Reduced pressure is transmitted further still through the shaped dressing bolster 532 so that reduced pressure delivered to the linear wound 512. At least at the early stages of the healing process, reduced pressure may also be realized through the linear wound 512 and into the subcutaneous tissue site 520. As such, reduced pressure may help close defects, such as subcutaneous void 522, and generally provides stability to the area. Reduced pressure delivered to the shaped dressing bolster 532 also develops the compressive force 524 that again may provide stability and therapy. The compressive force 524 is more than just at the top of the epidermis 514. The compressive force 524 extends down deeper and may be experienced at the level of the subcutaneous tissue site 520. The compressive force may help close defects and provide stability.

It may be desirable to apply the see-through wound treatment system 510 in the operating room and allow the see-through wound treatment system 510 to remain on the patient until adequate healing has taken place. In this regard, it may be desirable to form the sealing member 562, shaped dressing bolster 532, and any other layers from see-through materials that allow the healthcare provider to gain visual cues about the healing of the linear wound 512 and damaged subcutaneous tissue site 520 without having to remove the dressing assembly 530.

According to one illustrative embodiment, a see-through dressing assembly for use with a reduced-pressure system for treating a linear wound on a patient includes a closing dressing bolster for providing a closing force when under reduced pressure and a sealing member for covering the closing dressing bolster and providing a seal over the closing dressing bolster. The closing dressing bolster and sealing member are formed from see-through materials sufficient to allow perception of color from a point external to the see-through dressing assembly. The closing dressing bolster may include a top wall and a bottom wall. The top wall and bottom wall are coupled in a spaced relationship. The bottom wall includes a center portion, a first lateral portion, and a second lateral portion. A first closing member is formed on the first lateral portion, and a second closing member is formed on the second lateral portion. When placed under reduced pressure, the first closing member and the second closing member move towards each other.

According to one illustrative embodiment, a system for treating a wound on a patient with reduced pressure and that allows visual observation of the wound during treatment includes a dressing bolster for placing on a portion of the patient's epidermis over the wound. The dressing bolster is formed from a see-through material. The system further includes a sealing subsystem for providing a seal over the closing bolster and the patient's epidermis and a reduced-pressure subsystem for delivering a reduced pressure to the sealing subsystem. The sealing subsystem and reduced-pressure subsystem are operable to deliver reduced pressure to the dressing bolster. The dressing bolster, sealing subsystem, and reduced-pressure subsystem are operable to develop a directed force and to deliver reduced pressure to the wound. The sealing subsystem includes a see-through sealing member. The dressing bolster and sealing subsystem are operable to allow light to pass such that shades of color of the wound may be perceived from a place external to the system. The dressing bolster has a first surface, a second, inward-facing surface and includes an oblique extremity formed a portion of the dressing bolster. The dressing bolster is formed from a medical bolster material that has a density greater than 20 kg/m3. The dressing bolster has the characteristic of evenly distributing a directed force when under a reduced pressure.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

We claim:

1. A see-through dressing assembly for use with a reduced-pressure system for treating a linear wound on a patient, the see-through dressing assembly comprising:
    a closing dressing bolster for providing a closing force when under reduced pressure, the closing dressing bolster comprising:
        a top wall,
        a bottom wall, the top wall and bottom wall are coupled in a spaced relationship, the bottom wall having a center portion, a first lateral portion, and a second lateral portion,
        a first closing member formed on the first lateral portion, and
        a second closing member formed on the second lateral portion;
    a sealing member for covering the closing dressing bolster and providing a seal over the closing dressing bolster;
    wherein the closing dressing bolster and sealing member are formed from see-through materials sufficient to allow perception of color from a point external to the see-through dressing assembly; and
    wherein the geometry of the closing dressing bolster causes a bending moment to develop about the center portion when the closing dressing bolster is subject to reduced pressure, the bending moment causing the first closing member and second closing member to develop the closing force, and the closing force being directed downward and inward relative to the linear wound.

2. The see-through dressing assembly of claim 1 wherein the first closing member and second closing member are operable to move towards each other under reduced pressure.

3. The see-through dressing assembly of claim 1 wherein the sealing member comprises an sealing member made from a see-through elastomeric material.

4. The see-through dressing assembly of claim 1 wherein the closing dressing bolster comprises see-through silicone.

5. The see-through dressing assembly of claim 1 wherein the sealing member comprises a sealing member made from a see-through elastomeric material and the closing dressing bolster is formed of see-through silicone.

6. A dressing assembly for use with a reduced-pressure treatment system on a patient, the dressing assembly comprising:
    a closing dressing bolster for placing over a wound on the patient and for providing a closing force when under reduced pressure, the closing dressing bolster comprising:
        a top wall and a bottom wall, wherein the top wall and bottom wall are coupled in a spaced relationship, the bottom wall having a center portion, a first lateral portion, and a second lateral portion,
        a first closing member formed on the first lateral portion, and
        a second closing member formed on the second lateral portion;
    a sealing member for covering the closing dressing bolster and providing a seal over the closing dressing bolster and a patient's epidermis;
    a visual inspection device for visually detecting color of the wound on the patient from a location external to the dressing assembly, wherein the visual inspection device comprises a bolster material with structural elements spaced apart broadly enough to allow color to be perceived through the bolster material and a see-through sealing member; and
    wherein the closing dressing bolster comprises a gap between the first closing member and second closing member that forms a wicking material holder.

7. The dressing assembly of claim 6 wherein the visual inspection device comprises a see-through material used to form the sealing member and the closing dressing bolster comprises a see-through material.

8. The dressing assembly of claim 6 wherein the bolster material comprises a non-opaque foam.

9. The dressing assembly of claim 6 wherein the bolster material comprises a bolster mesh.

10. The dressing assembly of claim 6 wherein the visual inspection device further comprises a bolster window disposed on the bolster material such that when the bolster window is pressed against the bolster material by reduced pressure, color may be detected through the bolster material and bolster window.

11. The dressing assembly of claim 6 wherein the sealing member comprises a see-through elastomeric material.

12. The dressing assembly of claim 6 wherein the closing dressing bolster comprises silicone and the sealing member comprises a see-through elastomeric material.

* * * * *